United States Patent [19]

Geoghegan et al.

[11] Patent Number: 4,894,240

[45] Date of Patent: Jan. 16, 1990

[54] CONTROLLED ABSORPTION DILTIAZEM FORMULATION FOR ONCE-DAILY ADMINISTRATION

[75] Inventors: Edward J. Geoghegan; Seamus Mulligan, both of Athlone, Ireland; Donald E. Panoz, Tuckerstown, Bermuda

[73] Assignee: Elan Corporation plc, Athlone, Ireland

[21] Appl. No.: 121,225

[22] Filed: Nov. 16, 1987

Related U.S. Application Data

[63] Continuation-in-part of Ser. No. 684,661, Dec. 20, 1984, Pat. No. 4,721,619.

[51] Int. Cl.⁴ ................................................ A61K 9/16
[52] U.S. Cl. ...................................... 424/497; 424/490; 424/489
[58] Field of Search ............... 424/459, 462, 468, 473, 424/490, 497, 489

[56] References Cited

U.S. PATENT DOCUMENTS

| | | | |
|---|---|---|---|
| 4,230,687 | 10/1980 | Sair et al. | 514/965 |
| 4,263,273 | 4/1981 | Appelgren et al. | 424/19 |
| 4,499,066 | 2/1985 | Moro et al. | 424/22 |
| 4,555,398 | 11/1985 | Oda | 424/425 |
| 4,555,399 | 11/1985 | Hsiao | 424/80 |
| 4,592,753 | 6/1986 | Panoz | 604/897 |
| 4,600,645 | 7/1986 | Ghebre-Sellassie et al. | 424/19 |
| 4,609,542 | 9/1986 | Panoz et al. | 424/19 |
| 4,610,870 | 9/1986 | Jain et al. | 424/19 |
| 4,690,935 | 9/1987 | Taylor et al. | 524/211 |
| 4,721,619 | 1/1988 | Panoz et al. | 424/497 |

FOREIGN PATENT DOCUMENTS

| | | | |
|---|---|---|---|
| 0013262 | 7/1980 | European Pat. Off. | |
| 0077956 | 5/1983 | European Pat. Off. | |
| 2313915 | 1/1977 | France | |
| 59-10512A | 1/1984 | Japan | |
| 2039737 | 8/1980 | United Kingdom | 424/19 |

OTHER PUBLICATIONS

Chemical Abstracts, vol. 100, No. 18, Apr. 30, 1984, p. 367, abstract 145016c.

*Primary Examiner*—Thurman K. Page
*Assistant Examiner*—Leon R. Horne
*Attorney, Agent, or Firm*—Marla J. Church; Robert H. Falk

[57] ABSTRACT

A diltiazem pellet formulation for oral administration comprises a core of diltiazem or a pharmaceutically acceptable salt thereof in association with an organic acid, and a multi-layer membrane surrounding the core and containing a major proportion of a pharmaceutically acceptable film-forming, water insoluble synthetic polymer and a minor proportion of a pharmaceutically acceptable film-forming, water soluble synthetic polymer. The number of layers in the membrane and the ratio of the water soluble to water insoluble polymer being effective to permit release of the diltiazem from the pellet at a rate allowing controlled absorption thereof over a twenty four hour period following oral administration.

28 Claims, No Drawings

CONTROLLED ABSORPTION DILTIAZEM FORMULATION FOR ONCE-DAILY ADMINISTRATION

RELATED APPLICATIONS

This application is a continuation-in-part of Ser. No. 684,661 to Donald E. Panoz and Edward J. Geoghegan entitled "CONTROLLED ABSORPTION DILTIAZEM PHARMACEUTICAL FORMULATION" filed Dec. 20, 1984, having a priority of Dec. 22, 1983, based on Irish Patent Application No. 3,057/83; Ser. No. 684,661 issued on Jan. 26, 1988, as U.S. Pat. No. 4,721,619.

BACKGROUND OF THE INVENTION

This invention relates to a controlled absorption pharmaceutical formulation and, in particular, to a controlled absorption form of diltiazem for oral administration.

DESCRIPTION OF THE PRIOR ART

Diltiazem-cis-(+)-3-(acetyloxy)-5-[2-(dimethylamino)ethyl]-2,3-dihydro-2-(4-methoxyphenyl)-1,5-benzothiazepin-4(5H)-one, is a benzothiazine derivative possessing calcium antagonist activity. Diltiazem blocks the influx of calcium ions in smooth and cardiac muscle and thus exerts potent cardio-vascular effects. Diltiazem has been shown to be useful in alleviating symptoms of chronic heart disease, particularly angina pectoris and myocardial ischemia and hypertension, while displaying a low incidence of side effects. Diltiazem is conventionally administered in tablet form (30 mg or 60 mg) as diltiazem hydrochloride sold under the Trade Mark Carcizem (Marion Laboratories Inc.). Diltiazem in tablet form (30 mg) is also sold under the Trade Mark Herbesser (Tanabe Seiyaku). Diltiazem is also sold in capsule form.

Conventional diltiazem therapy starts with 30 mg administered 4 times daily. The dosage is gradually increased to 240 mg, given in divided doses three or four times daily, at one-to two- day intervals until an optimum response is obtained Diltiazem is extensively metabolized by the liver and excreted by the kidneys and in bile. According to professional use information issued by Marion Laboratories Inc., Cardizem is absorbed from the known tablet formulation to about 80% and is subject to an extensive first-pass effect, giving an absolute bioavailability, compared to intravenous administration, of about 40%. Single oral doses of 30 to 120 mg of Cardizem result in peak plasma levels 2-3 hours after administration. Detectable plasma levels occur within 30-60 minutes after administration indicating that Cardizem is readily absorbed.

The plasma elimination half-life following single or multiple administration is approximately 3-5 hours. Therapeutic blood levels of Cardizem are thought to be in the range of 50-200 ng/ml.

As stated above, conventional diltiazem capsules and tablets are administered three or four times daily. Such frequent drug administration may reduce patient compliance and produces irregular blood levels; thus adverse therapeutic effects can arise.

An article by McAuley, Bruce J. and Schroeder, John S. in Pharmacotherapy 2: 121, 1982 states that peak plasma levels of diltiazem occur within one hour with normal capsules and within 3 to 4 hours with sustained release tablets. However, the Applicants have found that peak plasma levels of diltiazem occurring within 3 to 4 hours following administration were incompatible with effective and efficacious twice-daily administration of diltiazem, and that peak plasma levels occurring within 6 to 9 hours as obtained in the case of the controlled absorption diltiazem formulation of the Applicants' co-pending U.S. patent application Ser. No. 684,661 filed Dec. 20, 1984, and incorporated herein by reference, satisfy accepted criteria for twice-daily administration of diltiazem, with preferred levels occurring within 8 to 9 hours. Furthermore, it will be appreciated peak plasma levels of diltiazem occurring within 3 to 4 hours are incompatible with effective and efficacious once-daily administration of diltiazem.

It is an object of the present invention to provide a controlled absorption diltiazem formulation suitable for once-daily administration and which is bioequivalent to known oral formulations of diltiazem.

DESCRIPTION OF THE INVENTION

Accordingly, the invention provides a diltiazem pellet formulation for oral administration, said pellet comprising a core of diltiazem or a pharmaceutically acceptable salt thereof in association with an organic acid, the diltiazem component and the organic acid being present in a ratio of from 20:1 to 1:1, and a multi-layer membrane surrounding said core and containing a major proportion of a pharmaceutically acceptable film-forming, water insoluble synthetic polymer and a minor proportion of a pharmaceutically acceptable film-forming, water soluble synthetic polymer, the number of layers in said membrane and the ratio of said water soluble to water insoluble polymer being effective to permit release of said diltiazem from said pellet at a rate allowing controlled absorption thereof over a twenty four hour period following oral administration, said rate being measured in vitro as a dissolution rate of said pellet, which when measured in a type 2 dissolution apparatus (paddle) according to U.S. Pharmacopoeia XXI in 0.05M KCl at pH 7.0 and at 100 r.p.m. substantially corresponds to the following dissolution pattern:

(a) from 0 to 35% of the total diltiazem is released after 2 hours of measurement in said apparatus;

(b) from 5 to 45% of the total diltiazem is released after 4 hours of measurement in said apparatus;

(c) from 30 to 75% of the total diltiazem is released after a total of 8 hours of measurement in said apparatus;

(d) from 60 to 95% of the total diltiazem is released after 13 hours of measurement in said apparatus; and (e) not less than 85% of the total diltiazem is released after 24 hours of measurement in said apparatus.

Whereas the formulation of patent application Ser. No. 684,661 is eminently suitable for twice-daily administration of diltiazem, the Applicants have found in the case of the present invention that peak plasma levels of 10 to 14 hours are essential in satisfying accepted criteria for once-daily administration of diltiazem, with preferred levels occurring within 12-14 hours. The present invention achieves this extension in time to peak plasma level as defined herein by Tmax.

The invention also provides a controlled absorption diltiazem formulation for oral administration, comprising pellets as hereinbefore defined, said formulation including a sufficient quantity of a rapid release form of diltiazem so as to have a dissolution rate which when measured in a type 2 dissolution apparatus (paddle) according to U.S. Pharmacopoeia XXI in 0.05 M KCl at pH 7.0 and at 100 r.p.m. substantially corresponds to the following dissolution pattern:

(a) from 5 to 35% of the total diltiazem is released after 2 hours of measurement in said apparatus;

(b) from 10 to 45% of the total diltiazem is released after 4 hours of measurement in said apparatus;

(c) from 30 to 75% of the total diltiazem is released after a total of 8 hours of measurement in said apparatus;

(d) from 60 to 95% of the total diltiazem is released after 13 hours of measurement in said apparatus; and (e) not less than 85% of the total diltiazem is released after 24 hours of measurement in said apparatus.

Preferably, the formulation comprises a blend of pellets as hereinbefore defined together with up to 25% by weight of said rapid release form of diltiazem.

Most preferably, the rapid release form of diltiazem comprises pellets as hereinbefore defined without said membrane.

Preferably, the diltiazem is in the form of a pharmaceutically acceptable salt thereof, more particularly the hydrochloride salt thereof.

The organic acid is preferably represented by one or more of the following acids: adipic acid, ascorbic acid, citric acid, fumaric acid, malic acid, succinic acid or tartaric acid. Especially preferred acids are fumaric acid and succinic acid. The diltiazem component and organic acid are preferably present in a ratio of from 10:1 to 2:1, more especially 5:1 to 3:1.

The core also optionally contains a lubricant which is represented by one or more of the following: sodium stearate, magnesium stearate, stearic acid or talc. The diltiazem and lubricant are preferably present in a ratio of from 5:1 to 100:1.

Preferably, the core comprises diltiazem or a pharmaceutically acceptable salt thereof and the associated organic acid embedded in a polymeric material. The polymeric material may be rapidly soluble in water or, alternatively, may be freely permeable to diltiazem and water.

The term water soluble polymer as used herein includes polymers which are freely permeable to water such as Eudragit R. L. Likewise, the term water insoluble polymer as used herein includes polymers which are slightly permeable to water such as Eudragit RS.

The polymeric material preferably consists solely of a water soluble polymer or a polymer which is freely permeable to diltiazem and water. Alternatively, the polymeric material of the core may include a minor proportion of a water insoluble polymer or a polymer which is slightly permeable to diltiazem and water. The ratio of water soluble/freely permeable to water insoluble/slightly permeable polymer is determined by the particular combination of polymers selected. However, in the case of a core including a water soluble polymer and a water insoluble polymer, the ratio of water soluble polymer to water insoluble polymer will normally be in the range of 1:1 to 50:1, more especially 3:1 to 9:1.

The water soluble polymer is suitably polyvinyl alcohol, polyvinylpyrrolidone, methyl cellulose, hydroxypropyl cellulose, hydroxypropylmethyl cellulose or polyethylene glycol or a mixture thereof. An especially preferred water soluble polymer is polyvinylpyrrolidone.

A suitable polymer which is freely permeable to diltiazem and water is a polymer sold under the Trade Mark EUDRAGIT RL.

The water insoluble polymer is suitably ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) or polyurethane or a mixture thereof.

A suitable polymer which is slightly permeable to diltiazem and water is a polymer sold under the Trade Mark EUDRAGIT RS or a polymer whose permeability is pH dependent and sold under the Trade Mark EUDRAGIT L, EUDRAGIT S or EUDRAGIT E.

EUDRAGIT polymers are polymeric lacquer substances based on acrylates and/or methacrylates.

Polymeric materials sold under the Trade Marks EUDRAGIT RL and EUDRAGIT RS are acrylic resins comprising copolymers of acrylic and methacrylic acid esters with a low content of quaternary ammonium groups and are described in the "EUDRAGIT" brochure of Messrs. Rohm Pharma GmbH (1985) wherein detailed physical-chemical data of these products is given. The ammonium groups are present as salts and give rise to the permeability of the lacquer films. EUDRAGIT RL and RS are freely permeable (RL) or slightly permeable (RS), respectively, independent of pH.

EUDRAGIT L is an anionic polymer synthesized from methacrylic acid and methacrylic acid methyl ester. It is insoluble in acids and pure water. It becomes soluble in a neutral to weakly alkaline milieu by forming salts with alkalis. The permeability of EUDRAGIT L is pH dependent. Above pH 5.0, the polymer becomes increasingly permeable. EUDRAGIT L is described in the "EUDRAGIT L" brochure of Messrs. Rohm Pharma GmbH (1986) wherein detailed physical-chemical data of the product is given.

The core suitably has between 50 and 200 layers of the core-forming materials and is built up in a manner known per se.

Preferably, the multi-layer arrangement of diltiazem, organic acid and polymeric material is built up on a central inert core, suitably consisting of a non-pareil bead or seed of sugar/starch having an average diameter in the range 0.4–0.8 mm, especially 0.6–0.71 mm, in a conventional coating pan. Alternatively, the diltiazem, organic acid and polymeric material may be built up on a central inert core as hereinbefore defined in an automated coating system, for example, a CF granulator.

The core may also include further components to those specified above such as a dispersing agent, glidant and/or surfactant.

The diltiazem, organic acid and optional other components are blended to form a homogenous powder. The blend is suitably passed through an appropriate mesh screen using a milling machine. In the case of coating in a conventional coating pan, alternate layers of a coating solution/suspension of the polymeric material and the powder are applied to the central inert core so as to build up the multi-layer arrangement of the active core. In the case of an automatic coating system, the coating solution/suspension of the polymeric material and the powder are applied simultaneously, in conventional manner. The coating solution/suspension of the polymeric material comprises one or more polymers dissolved/suspended in a suitable solvent or mixture of solvents. The concentration of the polymeric material in the coating solution/suspension is determined by the viscosity of the final solution/suspension. Preferably, between 10 and 40 parts of inert cores are used relative to the homogenous powder. The addition of a plasticizing agent to the polymeric solution/suspension may be necessary depending on the formulation to improve the elasticity and also the stability of the polymer film and to prevent changes in the polymer permeability over prolonged storage. Such changes could affect the drug release rate. Suitable plasticizing agents include polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil and varying percentages of acetylated monoglycerides.

Preferred coating materials include solutions/suspensions of the polymers cited for use in the application of the powder blend to the central inert core in a suitable organic/aqueous carrier medium.

The membrane of the film-forming polymer or mixture of polymers surrounding the core preferably has a major proportion of a water insoluble polymer and a minor proportion of a water soluble polymer, the ratio of water insoluble to water soluble polymer being determined by the inherent solubility characteristics of the polymer selected.

The membrane may also be composed of a proportion of a polymer which is slightly permeable to diltiazem and water and a proportion of a polymer which is freely permeable to diltiazem and water, the ratio of slightly permeable to freely permeable polymer being determined by the inherent permeability of the respective polymers. The terms "water soluble" and "water insoluble" polymer embrace such polymers as indicated above. A suitable combination of a polymer which is slightly permeable to diltiazem and water and a polymer which is freely permeable to ciltiazem and water is EUDRAGIT RS and EUDRAGIT RL in a ratio of from 1:1 to 50:1, especially 2:1 to 10:1. The membrane may also include a combination of water soluble/water insoluble polymers and polymers which are freely permeable/slightly permeable to diltiazem and water.

The membrane may also comprise a mixture of polymers that are water soluble, freely permeable, water insoluble, slightly permeable and polymers whose permeability/solubility is affected by pH.

Especially suitable polymers for the membrane include:

Polyvinylpyrrolidone, ethylcellulose, Eudragit RL, Eudragit L, Eudragit E, Eudragit S, cellulose acetate and polyvinyl alcohol. Commercially available ready-made polymeric solutions/suspensions are also especially preferred. These ready made solutions/suspensions may optionally contain plasticizing agents to improve the polymer film as described previously. Examples of readymade solutions/suspensions of polymeric material with or without plasticizing agent include Eudragit RL 30D, Eudragit L 30D, Eudragit E 12.5, Eudragit L 12.5 P, Eudragit E 12.5, Eudragit S 12.5P, Eudragit RL 12.5, Eudragit RS 12.5, (Eudragit being a Trade Mark of Rohm and Haas, whose technical brochures describe the differences between the products), Aquacoat (a Trade Mark of FMC Corporation) and Sure-lease (a Trade Mark of Colorcon Inc.).

The membrane may be built up by applying a plurality of coats of membrane polymer solution or suspension to the core as hereinafter described. The membrane solution or suspension contains the polymer(s) dissolved or suspended, respectively, in a suitable aqueous or organic solvent or mixture of solvents, optionally in the presence of a lubricant. Suitable lubricants are talc, stearic acid, magnesium stearate and sodium stearate. A particularly preferred lubricant is talc. The membrane, polymer or mixture of polymers may optionally include a plasticizing agent, the function and choice of which has been previously described.

Preferably, the number of coats of membrane solution or suspension applied is between 20 and 600. The dissolution rate achieved is proportionally slower as the number of membrane coats increases.

The membrane solution or suspension may be applied to the active cores in a conventional coating pan as indicated or, alternatively, using an automated system such as a CF granulator, for example a FREUND CF granulator, a GLATT fluidized bed processor, an AEROMATIC, a modified ACCELA-COTA or any other suitably automated bead coating equipment (FREUND, GLATT, AEROMATIC and ACCELA-COTA are all Trade Marks).

Preferably 2-25 ml of membrane solution/suspension is applied per coat per kilogram of active cores. In an automated system the total amount of membrane solution/ suspension applied to the active cores is the same as that applied in a conventional coating pan, except that the membrane solution/suspension is applied continuously.

Preferably, when a coating pan is used the membrane is applied at a rate of 25 coats/day until all of the coats have been applied. Between applications the pellets are dried for more than 12 hours at a temperature of 50-60° C., most suitably 55° C.

In an automated system the membrane is preferably applied at a rate which is equivalent to the application of 25 coats/day. After each application of this amount of membrane solution/suspension, the beads are dried at the temperature and for the length of time specified for coating in a coating pan.

In an automated coating system the rate of application of membrane solution/suspension is suitably 0.5-10 g/kg of cores/min. The rate of application of lubricant such as talc is also suitably 0.5-10 g/kg of cores/min.

The pellets may be filled into hard or soft gelatine capsules. The pellets may also be compressed into tablets using a binder and/or hardening agent commonly employed in tabletting such as microcrystalline cellulose sold under the Trade Mark "AVICEL" or a co-crystallised powder of highly modified dextrins (3% by weight) and sucrose sold under the Trade Mark "DI-PAC" in such a way that the specific dissolution rate of the pellets is maintained.

The invention will be further illustrated by the following Examples:

EXAMPLE 1

Diltiazem hydrochloride (40 kg), fumaric acid (10 kg) and talc (4 kg) were blended and milled through a suitable mesh screen so as to obtain a homogenous powder.

The powder was applied to starch/sugar seeds (0.6-0.71 mm diameter) (10 kg) using a FREUND CF granulator and a coating solution of:

9% polyvinylpyrrolidone in ethanol

A membrane was then applied to the active cores by spraying on a solution consisting of:

| | |
|---|---|
| 12.5% EUDRAGIT RS in acetone/isopropanol 40:60 | 40 parts by weight |
| 12.5% EUDRAGIT RL in acetone/isopropanol 40:60 | 10 parts by weight |
| Isopropanol | 50 parts by weight | while at the same time but separately dusting on talc (100 parts by weight) in conventional manner. The ratio of membrane solution to talc was 1:0.62 viz 0.62 grams of talc is applied per gram of membrane solution. A sufficient amount of membrane solution and talc was applied to 50 kg of active cores to achieve the following dissolution profile given below.

The finished pellets were dried to evaporate all solvents prior to performing the dissolution test. The dissolution rate of the pellets was tested by the method of the U.S. Pharmacopoeia XXI Paddle Method in 0.05M KCl, at pH 7.0 at 100 r.p.m.

The diltiazem hydrochloride was quantitatively determined using u.v. spectrophotometry at 237 nm. The dissolution rate was as follows:

| Time (h) | % Diltiazem Hydrochloride released |
|---|---|
| 2 | 2.3 |
| 4 | 17.7 |
| 8 | 49.0 |
| 13 | 76.5 |
| 24 | 95.7 |

EXAMPLE 2

Example 1 was repeated except that the application of membrane-forming suspension was continued until the following dissolution profile was obtained.

The dissolution rate of the pellets so prepared was determined according to the procedure of Example 1 and was found to be as follows:

| Time (h) | % Diltiazem Hydrochloride released |
|---|---|
| 2 | 0.8 |
| 4 | 13.8 |
| 8 | 52.6 |
| 13 | 80.4 |
| 24 | 98.1 |

EXAMPLE 3

Diltiazem hydrochloride (40 kg), fumaric acid (10 kg) and talc (4 kg) were blended and millec through a No. 50 mesh screen so as to obtain a homogenous powder.

The powder was applied to starch/sugar seeds (0.6–0.71 mm diameter) (10 kg) employing a granulator using a coating solution of:

9% polyvinylpyrrolidone in ethanol

A membrane was then applied to the active cores by spraying on a solution consisting of:

| | |
|---|---|
| 12.5% EUDRAGIT RS in acetone/isopropanol 40:60 | 41 parts by weight |
| 12.5% EUDRAGIT RL in acetone/isopropanol | 10 parts by weight |
| Isopropanol | 49 parts by weight | while at the same time but separately dusting on talc (100 parts by weight) in conventional manner. The ratio of membrane solution to talc applied was 1:0.62 viz 0.62 grams of talc is applied per gram of membrane solution. A sufficient amount of membrane solution (includes solvents) and talc was applied to 50 kg of active cores to achieve a dissolution rate of the pellets (determined in the manner set out in Example 1) as follows:

| Time (h) | % Diltiazem Hydrochloride released |
|---|---|
| 2 | 0.7 |
| 4 | 16.8 |
| 8 | 62.9 |
| 13 | 87.6 |
| 24 | 98.7 |

An amount of the sustained release pellets so prepared (85% by weight) was combined with an amount (15% by weight) of immediate release pellets corresponding to active cores without the membrane. The dissolution rate of the blend so prepared was determined and was found to be as follows:

| Time (h) | % Diltiazem Hydrochloride released |
|---|---|
| 2 | 24.70 |
| 4 | 40.30 |
| 8 | 70.10 |
| 13 | 89.30 |
| 24 | 98.90 |

EXAMPLE 4

Example 3 was repeated except that a sufficient amount of membrane solution (includes solvents) and magnesium stearate was applied to 50 kg of active cores, to achieve a dissolution rate of the pellets (determined in the manner set out in Example 1) as follows:

| Time (h) | % Diltiazem Hydrochloride released |
|---|---|
| 2 | 0.35 |
| 4 | 5.10 |
| 8 | 33.90 |
| 13 | 69.60 |
| 24 | 95.20 |

An amount of the pellets (85% by weight) so prepared was combined with an amount of active cores (15% by weight), which active cores release all of their diltiazem hydrochloride in approximately 30 minutes and the dissolution rate of the blend so prepared was measured in the manner set out in Example 1 and was found to be as follows:

| Time (h) | % Diltiazem Hydrochloride released |
|---|---|
| 2 | 11.30 |
| 4 | 15.75 |
| 8 | 49.50 |
| 13 | 81.85 |

| Time (h) | % Diltiazem Hydrochloride released |
|---|---|
| 24 | 96.95 |

EXAMPLE 5

Diltiazem hydrochloride (1.0 kg), adipic acid (0.5 kg) and talc (0.100 kg) were blended and milled through a No. 50 mesh screen so as to obtain a homogenous powder.

The powder was applied to starch/sugar seeds (0.6–0.71 mm diameter) (0.5 kg) in a standard coating pan using a coating solution of:

| 10% Polyvinylpyrrolidone in isopropanol | 80 parts by weight |
|---|---|
| 5% Ethylcellulose in isopropanol | 20 parts by weight |

The seeds were coated with a measured volume of coating solution followed by dusting on of a measured weight of the powder mix. The coated seeds were allowed to dry and the coating step repeated until all of the powder had been applied. The coated seeds defining active cores were then dried overnight to remove all traces of solvent.

The active cores of the pellets being prepared were then surrounded by a membrane solution consisting of:

| 5% Ethylcellulose in isopropanol | 90 parts by weight |
|---|---|
| 5% Polyvinylpyrrolidone in isopropanol | 10 parts by weight |

Each coat of membrane solution comprised 5 ml of solution per kg of coated seeds. After each coat had been applied the pellets were air dried in the coating pan.

The finished pellets were then subjected to a dissolution test. Prior to performing the dissolution test the pellets were dried to evaporate all of the solvent.

The dissolution rate of the pellets was tested by the method of U.S. Pharmacopoeia XXI (Paddle Method) according to the procedure of Example 1. The dissolution rate was as follows:

| Time (h) | % Diltiazem Hydrochloride released |
|---|---|
| 2 | 1.50 |
| 4 | 11.20 |
| 8 | 45.60 |
| 13 | 75.30 |
| 24 | 95.10 |

EXAMPLE 6

Example 5 was repeated except that the coating solution used was:

| 7.5% Cellulose acetate in isopropanol | 20 parts by volume |
|---|---|
| 7.5% Polyvinylpyrrolidone in isopropanol | 80 parts by volume |

| The membrane suspension used was | |
|---|---|
| 7.5% Polyvinylpyrrolidone in isopropanol | 10 parts by volume |
| 7.5% Cellulose acetate in isopropanol | 90 parts by volume |
| Isopropanol | 100 parts by volume |
| Talc | 100 parts by weight |

The dissolution rate of the pellets, which was measured according to the procedure followed in Example 1 was found to be:

| Time (h) | % Diltiazem Hydrochloride released |
|---|---|
| 2 | 0.10 |
| 4 | 8.50 |
| 8 | 42.10 |
| 13 | 65.70 |
| 24 | 94.50 |

EXAMPLE 7

Example 6 was repeated except that 0.75 kg starch/sugar seeds (0.5–0.6 mm) were used.

| The coating solution consisted of | |
|---|---|
| 5% EUDRAGIT RL in acetone/isopropanol 40:60 | 80 parts by weight |
| 5% EUDRAGIT RS in acetone/isopropanol 40:60 | 20 parts by weight |
| The membrane suspension consisted of | |
| 5% EUDRAGIT RL in acetone/isopropanol 40:60 | 20 parts by weight |
| 5% EUDRAGIT RS in acetone/isopropanol 40:60 | 40 parts by weight |
| 5% EUDRAGIT L in acetone/isopropanol 40:60 | 40 parts by weight |
| Talc | 100 parts by weight |

The membrane suspension was applied and the product dried as in Example 5.

The dissolution rate was as follows:

| Time (h) | % Diltiazem Hydrochloride released |
|---|---|
| 2 | 0.30 |
| 4 | 12.60 |
| 8 | 54.30 |
| 13 | 79.30 |
| 24 | 99.20 |

EXAMPLE 8

Diltiazem hydrochloride (3.067 kg) was blended together with an amount of pellets (39.932 kg) prepared in Example 3 along with Avicel pH101 (5.0 kg), cross-linked polyvinylpyrrolidone (1.75 kg) and magnesium stearate (0.25 kg).

The resulting blend was tabletted to obtain a tablet containing 240 mg diltiazem as the hydrochloride salt.

The dissolution rate of the tablets was tested by the method of the U.S. Pharmacopoeia XXI (Paddle Method) according to Example 1.

The dissolution rate was as follows:

| Time (h) | % Diltiazem hydrochloride % released |
|---|---|
| 2 | 22.6 |
| 4 | 41.5 |
| 8 | 69.8 |
| 13 | 89.5 |
| 24 | 98.9 |

EXAMPLE 9

Diltiazem Hydrochloride (3.0 kg), succinic acid (0.35 kg) and talc (0.3 kg) were blended and milled through a No. 100 mesh screen so as to obtain a homogenous powder.

The powder was applied to starch/sugar seeds (0.6–0.71 mm diameter) (0.75 kg) in a standard coating pan using a coating solution of:

9% polyvinyl pyrrolidone in isopropanol

The seeds were coated with a measured volume of coating solution followed by dusting on of a measured weight of the powder mix. The coated seeds were allowed to dry and the coating step repeated until all of the powder had been applied. The coated seeds defining the active cores of the pellet were then dried overnight to remove all traces of solvent.

The active cores of the pellet being prepared were then surrounded by a membrane by applying sequential coats of a suspension consisting of:

| | |
|---|---|
| 12.5% EUDRAGIT RS in acetone/isopropanol 40:60 | 53.33 parts by weight |
| 12.5% EUDRAGIT RL in acetone/isopropanol 40:60 | 13.33 parts by weight |
| Talc | 33.33 parts by weight |

After each coat had been applied the pellets were air dried in the coating pan.

Finished pellets were then subjected to a dissolution test. Prior to performing the dissolution test, the pellets were dried to evaporate all of the solvent. Application of the membrane-forming suspension and drying were continued until the following dissolution profile was obtained.

The dissolution rate of the pellets was tested by the method of U.S. Pharmacopoeia XXI (Paddle Method) in 0.05M KCl at pH 7.0 at 100 r.p.m.

The diltiazem hydrochloride was quantatatively determined using a uv spectrophotometer at 237 nm. The dissolution rate was as follows:

| Time (h) | % Diltiazem Hydrochloride released |
|---|---|
| 2 | 1.7 |
| 4 | 10.7 |
| 8 | 50.6 |
| 13 | 79.9 |
| 24 | 101.4 |

EXAMPLE 10

Pellets were prepared using the ingredients and manufacturing process of Example 9 and having the following dissolution profile.

| Time (h) | % Diltiazem Hydrochloride released |
|---|---|
| 2 | 16.7 |
| 4 | 26.9 |
| 8 | 60.6 |
| 13 | 81.7 |
| 24 | 96.5 |

If desired, the same dissolution profile as given in Example 10 can be obtained by blending a proportion (5–20% by weight) of active cores with pellets as prepared in Example 9.

PHARMACOLOGICAL DATA FOR DILTAZEM FORMULATIONS

In Vivo Performance:

Pharmacological Data for the Diltiazem Formulation of Example 1

The pellet formulation prepared in Example 1 was evaluated in vivo under steady state conditions.

A steady-state study was performed in 12 young healthy male volunteers, comparing the formulation of Example 1 with a reference product (conventional immediate release tablets). The formulation of Example 1 was administered as a single 240 mg encapsulated dose at 0 hours, while the reference was administered as a single 60 mg tablet at 0, 6, 12 and 18 hours (i.e. q.i.d.). Plasma was sampled out to 24 hours and the mean results were calculated and tabulated.

The data presented in Table 1 are from day 5 sampling.

TABLE 1

| Mean Diltiazem Concentrations (ng/ml) - Day 5 | | |
|---|---|---|
| Hour | Reference | Formulation of Example 1 |
| 0.0 | 104.08 | 74.83 |
| 0.50 | 104.17 | 75.25 |
| 1.00 | 140.75 | 72.17 |
| 2.00 | 165.42 | 71.75 |
| 3.00 | — | 72.67 |
| 4.00 | 139.83 | 88.42 |
| 6.00 | 107.00 | 95.42 |
| 6.50 | 93.42 | — |
| 7.00 | 107.42 | — |
| 8.00 | 143.58 | 96.92 |
| 10.00 | 138.00 | 107.50 |
| 12.00 | 94.42 | 106.75 |
| 12.50 | 77.42 | — |
| 13.00 | 87.83 | — |
| 13.50 | 92.58 | — |
| 14.00 | 109.42 | 109.17 |
| 16.00 | 109.00 | 107.75 |
| 18.00 | 82.33 | 96.25 |
| 18.50 | 81.45 | — |
| 19.00 | 94.00 | — |
| 20.00 | 120.33 | 85.00 |
| 22.00 | 117.75 | — |
| 24.00 | 98.92 | 71.08 |

DISCUSSION

The results of this in vivo comparison of the formulation of Example 1 against conventional immediate release tablets (reference) indicate the formulation of Example 1 to be bioequivalent (85%) to reference (100%). The formulation of Example 1 also exhibits reduced peak to trough fluctuations, thus enabling titration of the dose to safe, consistent and efficacious plasma levels, which is not always seen with more frequently administered immediate release forms of diltiazem.

However, the main distinguishing feature is the tmax (time to peak plasma levels) which is considered to be the single most important pharmacokinetic criterion for characterising a specific dosage frequency. The tmax for the formulation of Example 1 is 14.00 hours, thus indicating suitability thereof for once-daily administration, while the tmax for reference is 2.75 hours. Furthermore, when compared to the formulation of Example 1 of our patent application Ser. No. 684,661, a diltiazem formulation for twice-daily administration and having a tmax of 8.7 hours, the extension of tmax achieved with the formulation of the present invention becomes apparent.

Pharmacological Data for the Diltiazem Formulation of Example 2

METHOD

Subjects:

Six male volunteers participated in the study (Table 2). One subject (Subject 2) dropped out after the second leg of the study for reasons unrelated to participation in the study. All subjects were shown to be healthy during a prestudy physical examination. Volunteers denied use of any medication during the 14 days prior to study initiation.

TABLE 2

| | | Subject Demographics | | | |
|---|---|---|---|---|---|
| Subject Number | Subject Initials | Age Yrs | Height Cms | Weight (Kg) | Smoker |
| 1 | SF | 21 | 171.5 | 72.8 | Yes |
| 2 | NH | 21 | 173.0 | 65.0 | No |
| 3 | LH | 25 | 174.0 | 70.0 | No |
| 4 | PB | 21 | 172.0 | 61.5 | Yes |
| 5 | GG | 19 | 180.0 | 74.0 | Yes |
| 6 | TS | 40 | 165.0 | 77.0 | No |

Medication and Dosing

The following medication was used in the study:
(1) Reference 30 mg tablets
(2) Diltiazem 120 mg capsules prepared from a blend of sustained release pellets prepared in Example 2 with 5% of immediate release pellets viz the sustained release pellets without the membrane, hereinafter designated as the formulation of Example 2.

The reference was administered as a 30 mg dose at 0, 6, 12, and 18 hours. The formulation of Example 2 in capsule form was given as a single 120 mg dose at 0 hours.

The studies were designed as a randomized, balanced, single-dose two-way crossover comparison of the reference and the diltiazem formulation of Example 2.

The trial was initially divided into two 24-hour treatment periods. A third 24-hour treatment period was then performed. There were seven days separating each study period. At the time of study entry, subjects were randomly given a study number from 1 to 6, and assigned to treatment schedules based on that study number as shown in Table 3.

Volunteers arrived at the study site 10 to 12 hours before dosing and remained in a fasted state for at least 8 hours before and until 3 hours after dosing. Diet was standardized among treatment periods.

TABLE 3

| Subject Numbers | TREATMENT PERIODS | |
|---|---|---|
| | 1 | 2 |
| 1, 2, 3 | Reference | Formulation of Example 2 |
| 4, 5, 6 | Formulation of Example 2 | Reference |

Plasma diltiazem concentrations were determined by high performance liquid chromatography.

RESULTS

Plasma Diltiazem Concentrations

A summary of the mean results is presented in Table 4.

TABLE 4

| | Mean Diltiazem Concentrations (ng/ml) | |
|---|---|---|
| Time | Reference | Formulation of Example 2 |
| 0.0 | 0.0 | 0.0 |
| 0.5 | 4.02 ± 3.31 | — |
| 1.0 | 12.98 ± 4.78 | 6.10 ± 2.20 |
| 2.0 | 20.80 ± 9.36 | 6.88 ± 3.17 |
| 3.0 | 23.60 ± 11.15 | — |
| 4.0 | 22.00 ± 10.25 | 16.32 ± 7.23 |
| 6.0 | 15.68 ± 5.87 | 21.58 ± 13.33 |
| 6.5 | 15.82 ± 7.16 | — |
| 7.0 | 29.04 ± 15.29 | 30.60 ± 9.56 |
| 8.0 | 38.00 ± 10.46 | 35.80 ± 13.39 |
| 9.0 | — | 40.80 ± 18.90 |
| 10.0 | 32.00 ± 7.97 | 46.20 ± 20.78 |
| 12.0 | 21.60 ± 6.39 | 54.60 ± 26.43 |
| 12.5 | 18.40 ± 6.66 | — |
| 13.0 | 21.76 ± 9.10 | — |
| 14.0 | 33.60 ± 14.47 | 56.00 ± 25.42 |
| 16.0 | 34.60 ± 11.72 | 45.60 ± 16.96 |
| 18.0 | 26.80 ± 5.97 | 39.20 ± 13.99 |
| 18.5 | 26.60 ± 7.33 | — |
| 19.0 | 27.40 ± 12.92 | — |
| 20.0 | 38.20 ± 17.02 | 28.40 ± 5.27 |
| 22.0 | 34.20 ± 9.88 | — |
| 24.0 | 33.20 ± 14.86 | 22.80 ± 7.29 |
| 28.0 | 17.02 ± 4.75 | — |
| 36.0 | 2.58 ± 3.55 | 3.54 ± 3.38 |

DISCUSSION

The purpose of the studies carried out was to compare the pharmacokinetic profiles of a controlled absorption formulation of diltiazem according to the invention with divided doses of a reference product. The formulation of Example 2 was especially designed for once-daily administration of diltiazem and it was anticipated that this formulation would demonstrate a plasma profile consistent with this reduced dosage frequency.

The results of the study confirm the delayed and extended plasma profile of the formulation of Example 2. Although the product of Example 2 contains a proportion of immediate-release component (5%), the product demonstrated a significantly delayed time to peak plasma diltiazem concentrations compared with the reference. Mean trough levels were very similar for both products with no significant differences in mean blood concentrations at 24 hours post administration for the product of Example 2 relative to the reference, further emphasising the prolonged absorption nature of the formulation according to the invention.

The elimination characteristics of the formulation of Example 2 were also consistent with a once-daily plasma profile. The formulation of Example 2 showed a considerably slower apparent elimination rate and longer apparent half-life value compared with the reference.

Estimates of relative bioavailability showed the formulation of Example 2 to be more bioavailable than the reference product demonstrating 112.06% relative bioavailability based on 24 hour data.

The formulation of Example 2 attained a remarkably extended tmax of 13.20 hours after administration as compared to 2.30 hours for reference and 8.7 hours for the formulation of Example 1 of our patent application Ser. No. 684,661, which is a diltiazem formulation suitable for twice-daily administration. This extension in tmax thus shows the formulation of Example 2 to meet the criteria for once-daily administration and the overall results of the study demonstrate the achievement of a once-daily profile for the product of Example 2.

Pharmacological Data in Respect of the Formulation of Example 3

The blend of pellets prepared in Example 3 was filled into hard gelatine capsules so as to give capsules containing 120 mg diltiazem hydrochloride. A single dose of the capsules so prepared was compared with a single dose of pellets in capsule form and which pellets are prepared in accordance with Example 1 of our patent application Ser. No. 684,661 (twice-daily form of diltiazem) and identified hereinafter as "twice-daily formulation" administered as a single dose in six subjects. The two different formulations were tested in the same group of six subjects. The mean blood levels of the two formulations were determined and are shown in Table 5.

TABLE 5

| | Twice-daily Formulation | | Formulation of Example 3 |
|---|---|---|---|
| Time (h) | Blood Level (ng/ml) | Time (h) | Blood Level (ng/ml) |
| 0.00 | 0.00 | 0.00 | 0.00 |
| 1.00 | 0.00 | 1.00 | 11.20 |
| 2.00 | 2.17 | 2.00 | 12.30 |
| 4.00 | 29.67 | 4.00 | 17.97 |
| 5.00 | 52.33 | 5.00 | 22.67 |
| 6.00 | 63.67 | 6.00 | 28.67 |
| 7.00 | 69.00 | 7.00 | 32.33 |
| 8.00 | 69.50 | 8.00 | 36.17 |
| 9.00 | 62.50 | 9.00 | 38.50 |
| 10.00 | 53.83 | 10.00 | 44.50 |
| 12.00 | 38.67 | 12.00 | 41.67 |
| 14.00 | 27.17 | 14.00 | 35.33 |
| 16.00 | 20.17 | 16.00 | 28.33 |
| 18.00 | 15.22 | 18.00 | 23.00 |
| 20.00 | 12.95 | 20.00 | 18.33 |
| 24.00 | 7.70 | 24.00 | 12.77 |

Time of Maximum blood levels (tmax)

The time of maximum blood vessels (h) (tmax) was observed for each subject and each formulation.

The mean tmax values were as follows:

| Twice-daily formulation | Mean tmax = 7.17 | Based on 6 subjects |
|---|---|---|
| Formulation of Example 3 | Mean tmax = 10.67 | Based on 6 subjects |

DISCUSSION

In the study, the formulation of Example 3 was compared with a formulation prepared as per Example 1 of our Patent Application Ser. No. 684,661 which is an effective formulation for twice-daily administration of diltiazem. Whilst the "twice-daily" formulation achieves a notable extension in tmax (7.17 hours) as compared to conventional immediate release diltiazem, it does not exhibit a pharmacokinetic profile consistent with once-daily administration. However, the formulation of Example 3 demonstrates a lower peak to trough ratio than, while being bioequivalent (93.5%) to, the twice-daily formulation (100%). Most importantly, however, is the significantly extended tmax obtained (10.67 hours) with the formulation of Example 3, thus demonstrating an overall pharmacokinetic profile consistent with once-daily administration.

Pharmocological Data for the Diltiazem Hydrochloride Formulation Prepared in Example 4

The blend of pellets prepared in Example 4 was filled into hard gelatine capsules so as to give capsules containing 120 mg diltiazem hydrochloride. A single dose of the capsules so prepared was compared with conventional reference tablets (30 mg) hereinafter referred to as reference administered four times daily in six subjects. The two different formulations were tested in the same group of six subjects.

The mean blood levels of the two formulations were determined and are shown in Table 6.

TABLE 6

| Time (h) | Reference Blood Level (ng/ml) | Time (h) | Formulation of Example 4 Blood Level (ng/ml) |
|---|---|---|---|
| 0.00 | 0.00 | 0.00 | 0.00 |
| 0.50 | 4.33 | 0.50 | 0.00 |
| 1.00 | 6.40 | 1.00 | 10.42 |
| 1.50 | 12.52 | 2.00 | 17.63 |
| 2.00 | 18.65 | 4.00 | 15.07 |
| 4.00 | 22.17 | 6.00 | 21.22 |
| 6.00 | 12.07 | 7.00 | 23.38 |
| 6.50 | 10.62 | 8.00 | 27.30 |
| 7.00 | 21.47 | 10.00 | 33.67 |
| 7.50 | 30.83 | 12.00 | 39.83 |
| 8.00 | 29.00 | 14.00 | 40.83 |
| 10.00 | 31.17 | 16.00 | 33.83 |
| 12.00 | 16.97 | 20.00 | 25.17 |
| 12.50 | 15.65 | 24.00 | 20.13 |
| 13.00 | 15.42 | 36.00 | 4.62 |
| 13.50 | 25.00 | 0.00 | 0.00 |
| 14.00 | 29.50 | 0.00 | 0.00 |
| 16.00 | 30.30 | 0.00 | 0.00 |
| 18.00 | 21.93 | 0.00 | 0.00 |
| 18.50 | 25.00 | 0.00 | 0.00 |
| 18.90 | 26.33 | 0.00 | 0.00 |
| 19.50 | 29.65 | 0.00 | 0.00 |
| 20.00 | 37.83 | 0.00 | 0.00 |
| 22.00 | 35.33 | 0.00 | 0.00 |
| 24.00 | 28.83 | 0.00 | 0.00 |

Time of Maximum blood levels (tmax)

The time of maximum blood levels (h) (tmax) was observed for each subject and each formulation.

The mean tmax values were as follows:

| Reference Formulation of Example 4 | Mean tmax = 2.58 Mean tmax = 13.00 | Based on 6 subjects Based on 6 subjects |
|---|---|---|

DISCUSSION

The formulation of Example 4 demonstrated a remarkably extended in vivo tmax (13.00 hours) as compared to reference (2.58 hours). Furthermore, the formulation of Example 4 was bioequivalent (100%) to conventional immediate release tablets administered every six hours (100%). Based on this overall pharmacokinetic profile, the formulation of Example 4 is eminently suitable for once-daily oral administration.

What we claim is:

1. A diltiazem pellet formulation for oral administration, said pellet comprising a core to diltiazem or a pharmaceutically acceptable salt thereof in association with an organic acid, the diltiazem component and the organic acid being present in a ratio of from 20:1 to 1:1, and a multi-layer membrane surrounding said core and containing a major proportion of a pharmaceutically acceptable film-forming, water insoluble synthetic polymer and a minor proportion of a pharmaceutically acceptable film-forming, water soluble synthetic polymer, the number of layers in said membrane and the ratio of said water soluble to water insoluble polymer being effective to permit release of said diltiazem from said pellet at a rate allowing controlled absorption thereof over a twenty four hour period following oral administration, said rate being measured in vitro as a dissolution rate of said pellet, which when measured in a type 2 dissolution apparatus (paddle) according to U.S. Pharmacopoeia XXI in 0.05M KCl at pH 7.0 and at 100 r.p.m. substantially corresponds to the following dissolution pattern:
   (a) from 0 to 35% of the total diltiazem is released after 2 hours of measurement in said apparatus;
   (b) from 5 to 45% of the total diltiazem is released after 4 hours of measurement in said apparatus;
   (c) from 30 to 75% of the total diltiazem is released after a total of 8 hours of measurement in said apparatus;
   (d) from 60 to 95% of the total diltiazem is released after 13 hours of measurement in said apparatus; and
   (e) not less than 85% of the total diltiazem is released after 24 hours of measurement in said apparatus.

2. A pellet formulation according to claim 1, wherein the organic acid is selected from the group consisting of one or more of the following acids: adipic acid, ascorbic acid, citric acid, fumaric acid, malic acid, succinic acid and tartaric acid.

3. A pellet formulation according to claim 1, wherein the diltiazem or pharmaceutically acceptable salt thereof and organic acid are present in a ratio of from 10:1 to 2:1.

4. A pellet formulation according to claim 1, wherein the diltiazem or pharmaceutically acceptable salt thereof and organic acid are present in a ratio of 5:1 to 3:1.

5. A pellet formulation according to claim 1, wherein the core includes a lubricant selected from the group consisting of one or more of the following: sodium stearate, magnesium stearate, stearic acid and talc.

6. A pellet formulation according to claim 5, wherein the diltiazem and lubricant are present in a ratio of from 5:1 to 100:1.

7. A pellet formulation according to claim 1, wherein the core comprises
   (a) a powder mixture containing diltiazem or a pharmaceutically acceptable salt thereof, an organic acid selected from the group consisting of adipic acid, ascorbic acid, citric acid, fumaric acid, malic acid, succinic acid and tartaric acid, and
   (b) a polymeric material containing a major proportion of a pharmaceutically acceptable water soluble synthetic polymer and a minor proportion of a pharmaceutically acceptable water insoluble synthetic polymer, said core comprising layers of said powder mixture and said polymeric material superimposed one upon the other and said polymeric material being present in an amount effective to ensure that all of said powder mixture is coated into said core.

8. A pellet formulation according to claim 7, wherein the water soluble polymer is selected from the group consisting of polyvinyl alcohol, polyvinylpyrrolidone, methyl cellulose, hydroxypropyl cellulose, hydroxypropylmethyl cellulose and polyethylene glycol or a mixture thereof.

9. A pellet formulation according to claim 7, wherein the water soluble polymer is replaced by a polymeric material which is freely permeable to diltiazem and water and comprises a copolymer of acrylic and methacrylic acid esters.

10. A pellet formulation according to claim 7, wherein the water insoluble polymer is selected from the group consisting of ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) and polyurethane or a mixture thereof.

11. A pellet formulation according to claim 7, wherein the water insoluble polymer is replaced by a polymeric material which is slightly permeable to diltiazem and water and comprises a copolymer of acrylic and methacrylic acid esters.

12. A pellet formulation according to claim 7, wherein the diltiazem, organic acid and polymeric material are built up on an inert core.

13. A pellet formulation according to claim 12, wherein the inert core is a non-pareil bead or seed of sugar/starch having an average diameter in the range 0.4–0.8 mm.

14. A pellet formulation according to claim 1, wherein the core includes one or more additional components selected from the group consisting of a dispersing agent, aglidant and a surfactant.

15. A pellet formulation according to claim 1, wherein the water insoluble polymer of the membrane is selected from the group consisting of ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) and polyurethane or a mixture thereof.

16. A pellet formulation according to claim 1, wherein the water soluble polymer of the membrane is selected from the group consisting of polyvinyl alcohol, polyvinylpyrrolidone, methyl cellulose, hydroxypropyl cellulose, hydroxypropylmethyl cellulose and polyethylene glycol or a mixture thereof.

17. A pellet formulation according claim 1, wherein the water insoluble polymer of the membrane is replaced by a major proportion of a polymer which is slightly permeable to diltiazem and water and the water soluble polymer of the membrane is replaced by a minor proportion of a polymer which is freely permeable to diltiazem and water.

18. A pellet formulation according to claim 17, wherein each of the slightly permeable and freely permeable polymers comprises a copolymer of acrylic and methacrylic acid esters having the desired permeability characteristics.

19. A pellet formulation according to claim 1, which includes a plasticizing agent selected from the group consisting of polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil and an acetylated monoglyceride.

20. A pellet formulation according to claim 1, which contains diltiazem hydrochloride as the active ingredient.

21. A controlled absorption diltiazem formulation for oral administration comprising pellets as claimed in claim 1, said formulation including a sufficient quantity of a rapid release form of diltiazem so as to have a dissolution rate which when measured in a type 2 dissolution apparatus (paddle) according to U.S. Pharmacopoeia XXI in 0.05M KCl at pH 7.0 and at 100 r.p.m. substantially corresponds to the following:
 (a) from 5 to 35% of the total diltiazem is released after 2 hours of measurement in saio apparatus;
 (b) from 10 to 45% of the total diltiazem is released after 4 hours of measurement in said apparatus;
 (c) from 30 to 75% of the total diltiazem is released after a total of 8 hours of measurement in said apparatus;
 (d) from 60 to 95% of the total diltiazem is released after 13 hours of measurement in said apparatus; and
 (e) not less than 85% of the total diltiazem is released after 24 hours of measurement in said apparatus.

22. A controlled absorption diltiazem formulation according to claim 21, wherein up to 25% by weight of the formulation is the rapid release form of diltiazem.

23. A controlled absorption diltiazem formulation according to claim 22, wherein the rapid release form of diltiazem comprises a core of diltiazem or a pharmaceutically acceptable salt thereof in association with an organic acid, the diltiazem component and the organic acid being present in a ratio of from 20:1 to 1:1.

24. A capsule or tablet comprising a formulation of pellets according to claim 1.

25. A capsule or tablet comprising a formulation of pellets according to claim 21.

26. A diltiazem pellet formulation for oral administration, said pellet comprising a core of diltiazem or a pharmaceutically acceptable salt thereof in association with an organic acid, the diltiazem component and the organic acid being present in a ratio of from 20:1 to 1:1, and a multi-layer membrane surrounding said core and containing a major proportion of a pharmaceutically acceptable film-forming, water insoluble synthetic polymer and a minor proportion of a pharmaceutically acceptable film-forming, water soluble synthetic polymer, the number of layers in said membrane and the ratio of said water soluble to water insoluble polymer being effective to permit release of said diltiazem from said pellet at a rate allowing controlled absorption thereof over a twenty four hour period following oral administration, said rate being measured in vivo and having a Tmax between 10 and 14 hours.

27. A pellet formulation according to claim 26 wherein Tmax is between 12 and 14 hours.

28. A diltiazem pellet formulation for oral administration, said pellet comprising a core of diltiazem or a pharmaceutically acceptable salt thereof in association with an organic acid, the diltiazem component and the organic acid being present in a ratio of from 20:1 to 1:1, and a multi-layer membrane surrounding said core and containing a major proportion of a pharmaceutically acceptable film-forming, water insoluble synthetic polymer and a minor proportion of a pharmaceutically acceptable film-forming, water soluble synthetic polymer, the number of layers in said membrane and the ratio of said water soluble to water insoluble polymer being effective to permit release of said diltiazem from said pellet at a rate allowing controlled absorption thereof over a twenty four hour period following oral administration, said rate being measured in vitro as a dissolution rate of said pellet, which when measured in a type 2 dissolution apparatus (paddle) according to U.S. Pharmacopoeia XXI in 0.05M KCl at pH 7.0 and at 100 r.p.m. substantially corresponds to a dissolution pattern wherein after a total of 8 hours of measurement in said apparatus from 30 to 75% of the total diltiazem is released from said pellet and wherein after a total of 24 hours of measurement in said apparatus not less than 85% of the total diltiazem is released from said pellet.

* * * * *